United States Patent
Matsumoto et al.

(10) Patent No.: US 11,237,107 B2
(45) Date of Patent: *Feb. 1, 2022

(54) FLUORESCENCE IMAGE ANALYZING APPARATUS, IMAGE PROCESSING METHOD OF FLUORESCENCE IMAGE, AND COMPUTER PROGRAM

(71) Applicant: SYSMEX CORPORATION, Kobe (JP)

(72) Inventors: Shohei Matsumoto, Kobe (JP); Shruti Sharma, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/792,483

(22) Filed: Feb. 17, 2020

(65) Prior Publication Data

US 2020/0249165 A1 Aug. 6, 2020

Related U.S. Application Data

(63) Continuation of application No. 15/951,393, filed on Apr. 12, 2018, now Pat. No. 10,605,731.

(30) Foreign Application Priority Data

Apr. 14, 2017 (JP) .............. JP2017-080851

(51) Int. Cl.
*G01N 21/64* (2006.01)
*G06T 7/00* (2017.01)
(Continued)

(52) U.S. Cl.
CPC ....... *G01N 21/6428* (2013.01); *C12Q 1/6841* (2013.01); *G01N 21/6456* (2013.01);
(Continued)

(58) Field of Classification Search
CPC ............ G01N 21/6428; G01N 21/008; G01N 21/6456; G06T 7/0012; G06T 7/0002;
(Continued)

(56) References Cited

U.S. PATENT DOCUMENTS

| 2002/0146734 A1 | 10/2002 | Ortyn et al. |
| 2012/0097864 A1 | 4/2012 | Takahashi et al. |

(Continued)

FOREIGN PATENT DOCUMENTS

| JP | 2005-515408 A | 5/2005 |
| JP | 2008-518587 A | 6/2008 |

(Continued)

OTHER PUBLICATIONS

Siu et al., "Application of tri-colour, dual fusion fluorescence in situ hybridization (FISH) system for the characterization of BCR-ABL1 fusion in chronic myelogenous leukaemia (CML) and residual disease monitoring," BMC Blood Disorders, Biomed Central Ltd., vol. 9, No. 4, Jul. 7, 2009, pp. 1-6, London, GB.

(Continued)

*Primary Examiner* — Michael C Bryant

(74) *Attorney, Agent, or Firm* — Crowell & Moring LLP

(57) ABSTRACT

Disclosed is a fluorescence image analyzing apparatus including a light source that emits light to a sample including a plurality of cells labeled with a fluorescent dye at a target site, an imaging unit that captures a fluorescence image of each of the cells that emit fluorescence by being irradiated with the light, a processing unit that processes the fluorescence image captured by the imaging unit, and a display unit (Continued)

that displays the fluorescence image processed by the processing unit. The processing unit performs an extraction process of extracting, for each cell, a plurality of bright spots in the fluorescence image including the target site, a changing process of changing a pixel value of each of the plurality of extracted bright spots based on the pixel value of each bright spot, and a display process of displaying the fluorescence image whose pixel value is changed on the display unit.

21 Claims, 10 Drawing Sheets

(51) Int. Cl.
    *C12Q 1/6841* (2018.01)
    *G06T 5/00* (2006.01)
    *G02B 21/00* (2006.01)
(52) U.S. Cl.
    CPC ....... *G02B 21/008* (2013.01); *G02B 21/0076* (2013.01); *G06T 5/008* (2013.01); *G06T 7/0012* (2013.01); *G01N 2021/6439* (2013.01); *G01N 2021/6441* (2013.01); *G06T 2207/10024* (2013.01); *G06T 2207/10056* (2013.01); *G06T 2207/10064* (2013.01); *G06T 2207/30024* (2013.01); *G06T 2207/30072* (2013.01)
(58) Field of Classification Search
    CPC . G06T 2207/30072; G06T 2207/10024; G06T 2207/30024; G06T 2207/10064; G06T 2207/10056
    See application file for complete search history.

(56) References Cited

U.S. PATENT DOCUMENTS

| | | |
|---|---|---|
| 2014/0056505 A1 | 2/2014 | Hoyt |
| 2014/0072195 A1 | 3/2014 | Zhang et al. |
| 2014/0205173 A1 | 7/2014 | Padfield et al. |

FOREIGN PATENT DOCUMENTS

| | | |
|---|---|---|
| JP | 2010-500573 A | 1/2010 |
| JP | 2016-507229 A | 3/2016 |
| KR | 10-2008-0063280 A | 7/2008 |
| KR | 10-2009-0074155 A | 7/2009 |
| WO | WO02/093130 | 11/2002 |
| WO | 2006/036735 A2 | 4/2006 |
| WO | 2008/019299 A2 | 2/2008 |
| WO | 2010/150468 A1 | 12/2010 |
| WO | 2014/031735 A1 | 2/2014 |
| WO | WO2016/194338 | 12/2016 |

OTHER PUBLICATIONS

Pajor et al., "State-of-the-art FISHing: Automated Analysis of Cytogenetic Aberrations in Interphase Nuclei," Cytometry. Part A, vol. 81A, No. 8, Jun. 13, 2012, pp. 649-663.
Shi et al., "A Parallel Fish Image Processing Pipeline of High-Throughput Chromosomal Analysis," 2015 7th International Conference on Information Technology in Medicine and Education (ITME), IEEE, Nov. 13, 2015, pp. 337-342.
Communication pursuant to Article 94(3) EPC dated Mar. 13, 2020 in a counterpart European patent application No. 18166770.0.
Japanese Office Action dated Jan. 5, 2021 in a counterpart Japanese patent application No. 2017-080851.
Communication pursuant to Article 94(3) EPC dated Jul. 20, 2021 in a counterpart European patent application No. 18166770.0.

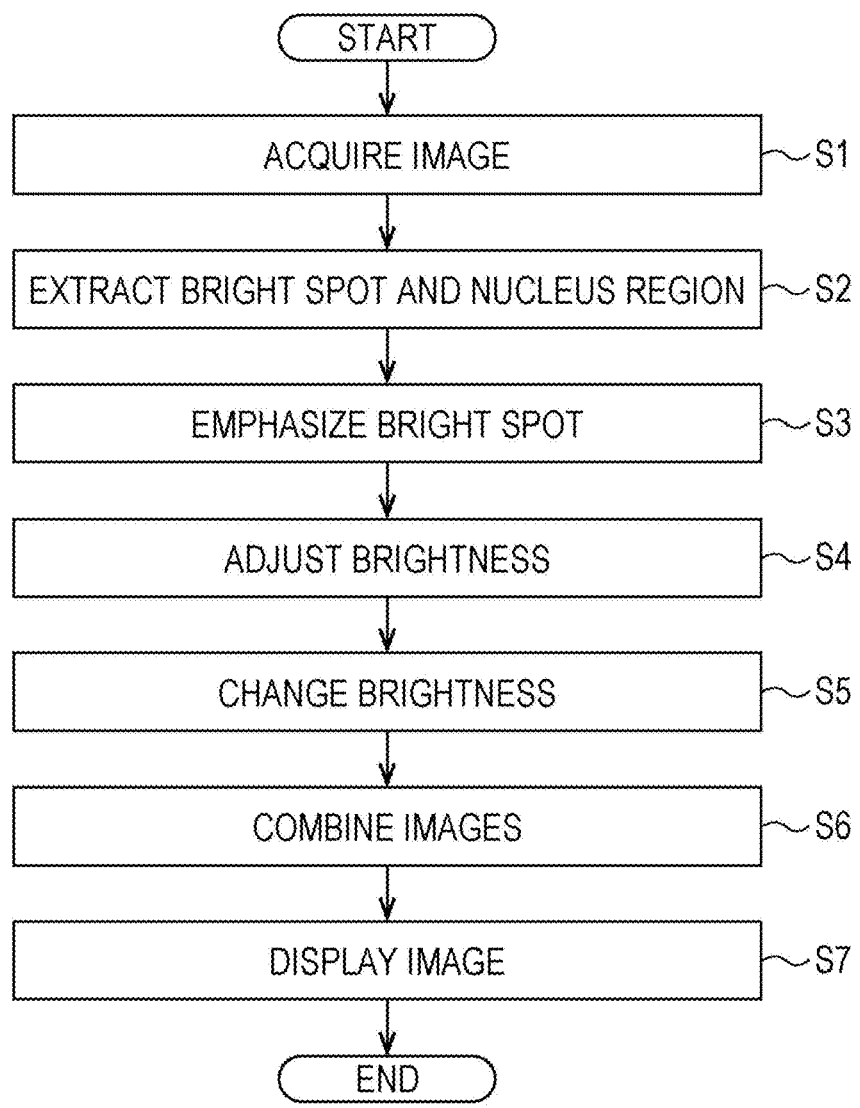

FLUORESCENCE IMAGE ANALYZING APPARATUS, IMAGE PROCESSING METHOD OF FLUORESCENCE IMAGE, AND COMPUTER PROGRAM

CROSS REFERENCE TO RELATED APPLICATIONS

This application is a continuation application of non-provisional U.S. patent application Ser. No. 15/951,393, filed on Apr. 12, 2018, which claims priority from prior Japanese Patent Application No. 2017-080851, filed on Apr. 14, 2017 entitled "FLUORESCENCE IMAGE ANALYZING APPARATUS, IMAGE PROCESSING METHOD OF FLUORESCENCE IMAGE, AND COMPUTER PROGRAM". The entirety of all of related applications are hereby incorporated by reference.

TECHNICAL FIELD

The present invention relates to a fluorescence image analyzing apparatus, an image processing method of a fluorescence image, and a computer program.

BACKGROUND

WO 2003/048300 discloses a method for treating cells when a flow cytometer or the like is applied for detection in a fluorescence in situ hybridization method (FISH method). In the FISH method, first, a pretreatment for hybridizing a fluorescently labeled probe to the base sequence of a target site present in the nucleus of a cell is performed to fluorescently label the target site. Subsequently, a fluorescence signal (bright spot) generated from the fluorescently labeled probe is detected.

In the FISH method, the fluorescence image is captured with a fluorescence microscope, an imaging flow cytometer, or the like. However, even in the case where the same fluorescently labeled probe is used, the brightness may be different between bright spots in one fluorescence image due to variations in pretreatment. Also, since cells take a three-dimensional shape in a flow cell of a flow cytometer, the brightness of a plurality of bright spots in one captured fluorescence image may be different from each other depending on the position (depth) of the bright spot when light is radiated thereto, for example, depending on whether the bright spot is present on the surface of the nucleus or near the center of the nucleus. As described above, the brightness of bright spots may vary in one fluorescence image when a fluorescence image of a cell is captured in a flow cytometer. Therefore, when an operator checks the presence or absence of a bright spot in the fluorescence image captured by a flow cytometer in the FISH method, there is a case where a darker bright spot cannot be detected.

Furthermore, in a multicolor FISH method, by using a probe labeled with a green fluorescent dye and a probe labeled with a red fluorescent dye, the presence or absence of a fused bright spot in which the two probes are combined by being adjacent to each other and in which yellow fluorescence is emitted is detected. Specifically, a fused bright spot is detected by superimposing a fluorescence image obtained by imaging the green fluorescent dye and a fluorescence image obtained by imaging the red fluorescent dye. However, as described above, in one fluorescence image captured in a flow cytometer, the brightness of a plurality of bright spots may vary. Therefore, there is a problem that, when confirming a fused bright spot in a fluorescence image captured by using a flow cytometer in the multicolor FISH method, for example, in the case where a certain red bright spot is dark and a green bright spot adjacent thereto is bright, the red bright spot is overwhelmed by the green bright spot and the operator cannot determine that the bright spot is a fused bright spot when two fluorescence images are superimposed.

SUMMARY OF THE INVENTION

The scope of the present invention is defined solely by the appended claims, and is not affected to any degree by the statements within this summary.

A first aspect of the present invention relates to a fluorescence image analyzing apparatus. A fluorescence image analyzing apparatus (1) according to this aspect includes a light source (120 to 123) that emits light to a sample (10) including a plurality of cells labeled with a fluorescent dye at a target site, an imaging unit (160) that captures a fluorescence image of each of the cells that emit fluorescence by being irradiated with the light, a processing unit (11) that processes the fluorescence image captured by the imaging unit (160), and a display unit (13) that displays the fluorescence image processed by the processing unit (11). The processing unit (11) performs an extraction process of extracting, for each cell, a plurality of bright spots in the fluorescence image including the target site, a changing process of changing a pixel value of each of the plurality of extracted bright spots based on the pixel value of the bright spot, and a display process of displaying the fluorescence image whose pixel value has been changed on the display unit.

A second aspect of the present invention relates to an image processing method of a fluorescence image in which a fluorescence image of a cell obtained by measuring a sample (10) including a plurality of cells in which a target site is labeled with a fluorescent dye is processed. The image processing method according to this aspect includes an extraction step of extracting, for each cell, a plurality of bright spots in the fluorescence image including the target site, and a changing step of changing a pixel value of each of the plurality of extracted bright spots based on the pixel value of the bright spot.

A third aspect of the present invention relates to computer program for causing a computer to execute image processing of a fluorescence image of a cell acquired by measuring a sample (10) including a plurality of cells in which a target site is labeled with a fluorescent dye. The image processing of the computer program according to this aspect includes an extraction process of extracting, for each cell, a plurality of bright spots in the fluorescence image including the target site, and a changing process of changing a pixel value of each of the plurality of extracted bright spots based on the pixel value of the bright spot.

According to the first to third aspects of the present invention, even when a light bright spot having high pixel values and a dark bright spot having low pixel values present in one fluorescence image of a cell from which the bright spots have been extracted, the pixel values of the dark bright spot are enhanced in a changing process (changing step) such that the difference between the pixel values of the dark bright spot and the light bright spot is reduced. Therefore, it becomes easier for an operator or the like to recognize a dark bright spot by visual observation in image observation of each fluorescence image. In addition, as a result of the pixel values of the dark bright spot being enhanced in a changing process (changing step) such that the difference between the pixel values of the dark bright spot and the light bright spot is reduced for each fluorescence image, in the analysis of a composite image in which a plurality of fluorescence images are combined, a plurality of bright spots overlap with each other at a fused bright spot in which bright spots of the fluorescence images overlap each other, in a state in which the difference in pixel value is reduced. Therefore, determination of whether or not a spot is a fused bright spot becomes easier, and thus it becomes easier for an operator or the like to detect a fused bright spot by visual observation. As described above, according to the present invention, even in the case where a light bright spot having high pixel values and a dark bright spot having low pixel values are present in one fluorescence image, confirmation of a bright spot in image observation of each fluorescence image and detection of a fused bright spot in analysis of a composite image of a plurality of fluorescence images can be performed easily.

BRIEF DESCRIPTION OF THE DRAWINGS

FIG. 3 is a flowchart for describing an operation of a processing unit;

DETAILED DESCRIPTION OF THE PREFERRED EMBODIMENTS

Hereinafter, embodiments of the present disclosure will be described in detail with reference to attached drawings. In the following embodiment, the present disclosure is applied to an apparatus in which a sample subjected to a pretreatment of hybridizing a target site (target sequence) present in the nucleus of a cell with a nucleic acid probe (hereinafter simply referred to as a probe) including a nucleic acid sequence having a sequence complementary to the target sequence and labeled with a fluorescent dye is measured and a fluorescence image acquired for each cell among a plurality of cells in the sample is analyzed.

In one example of this embodiment, analysis of chromosomal abnormalities by a fluorescence in situ hybridization (FISH) method is performed by, for example, a flow cytometer (e.g., imaging flow cytometer), a fluorescence microscope, or the like. In the following embodiment, as an example, an embodiment in which a BCR gene on chromosome 22 and an ABL gene on chromosome 9 are set as target sites in a nucleic acid, and cells having a translocation (a BCR/ABL fusion gene, also referred to as a Philadelphia chromosome: t (9; 22) (q34.12; q11.23)) between chromosome 9 and chromosome 22 observed in chronic myelogenous leukemia are measured and analyzed will be described. Chromosomal abnormalities detected by the fluorescence image analyzing apparatus are not limited as long as the abnormalities can be detected by the FISH method. Examples of chromosomal abnormalities include translocations, deletions, inversions, and duplications. Specific examples of the chromosomal abnormalities include chromosomal abnormalities associated with loci such as BCR/ABL fusion gene and ALK gene.

In the following embodiment, cells to be measured are not limited as long as the cells are nucleated cells. For example, the cells may be nucleated cells in a specimen collected from a subject, and may be preferably nucleated cells in a blood specimen. In this specification and the like, the sample is a cell suspension to be subjected to measurement including cells derived from a specimen including a target site hybridized with a probe. The sample includes a plurality of cells. The number of the plurality of cells are at least $10^2$ or more, preferably $10^3$ or more, more preferably $10^4$ or more, further preferably $10^5$ or more, and still more preferably $10^6$ or more.

In this embodiment, an abnormal cell refers to a cell having a chromosomal abnormality. Examples of abnormal cells include tumor cells such as cancer cells. Preferable examples of abnormal cells include hematopoietic tumor cell such as leukemia and cancer cells such as lung cancer.

Figure 1:
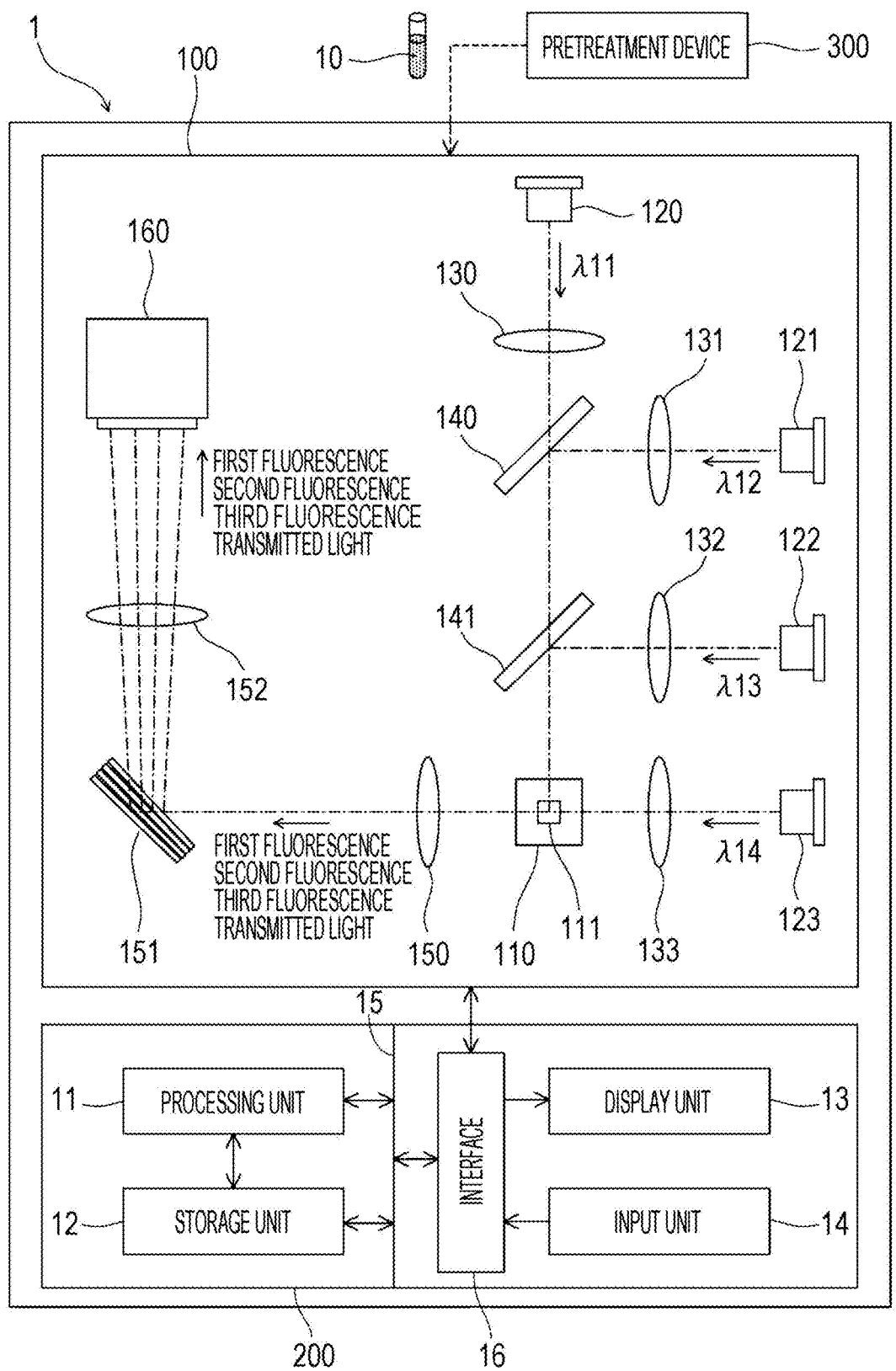
FIG. 1 is a schematic diagram showing a configuration of an embodiment of a fluorescence image analyzing apparatus.

FIG. 1 shows a schematic configuration of a fluorescence image analyzing apparatus 1 of this embodiment. The fluorescence image analyzing apparatus 1 shown in FIG. 1 includes a measurement device 100 and an image processing device 200 for processing a fluorescence image, and measures and analyzes a sample 10 prepared by a pretreatment by a pretreatment device 300.

An operator collects nucleated cells that are measurement target cells by, for example, centrifugally separating a blood specimen, collected from a subject, by using a cell separation medium such as Ficoll. In collecting the nucleated cells, the nucleated cells may be collected by hemolyzing erythrocytes or the like by using a hemolyzing agent to leave nucleated cells instead of collecting the nucleated cells by centrifugation. The pretreatment device 300 includes a mixing container for mixing the nucleated cell suspension acquired by centrifugation or the like with a reagent, a dispensing unit for dispensing the nucleated cell suspension and reagent to the mixing container, a heating unit for heating the mixing container, and the like. The pretreatment device 300 performs a pretreatment including a step of labeling a target site in a cell collected from a subject with a fluorescent dye and a step of staining the nucleus of the cell with a nuclear dye, and thus prepares a sample 10. Specifically, in the step of labeling a target site with a fluorescent dye, the target sequence and a probe including a nucleic acid sequence having a sequence complementary to the target sequence and labeled with a fluorescent dye are hybridized.

In the FISH method, a target site on a chromosome is detected by using one or more fluorescent dyes. Preferably, in the FISH method, two or more fluorescent dyes are used to detect a target site on a first chromosome and a target site on a second chromosome ("first" or "second" is a concept of a comprehensive number and does not indicate a chromosome number). For example, a probe that hybridizes with a BCR locus is a nucleic acid having a sequence complementary to the base sequence of the BCR locus and is labeled with a first fluorescent dye that generates a first fluorescence of a wavelength $\lambda 21$ by being irradiated with light of a wavelength $\lambda 11$. By using this probe, the BCR locus is labeled with the first fluorescent dye. A probe that hybridizes with an ABL locus is a nucleic acid having a sequence complementary to the base sequence of the ABL locus and is labeled with a second fluorescent dye that generates a second fluorescence of a wavelength $\lambda 22$ by being irradiated with light of a wavelength $\lambda 12$. By using this probe, the ABL locus is labeled with the second fluorescent dye. The nucleus is stained with a nuclear dye that generates a third fluorescence of a wavelength of $\lambda 23$ by being irradiated with light of a wavelength $\lambda 13$. The light of wavelength $\lambda 11$, the light of wavelength $\lambda 12$, and the light of wavelength $\lambda 13$ are so-called excitation light.

More specifically, the pretreatment device 300 performs a treatment for immobilizing cells so that the cells do not contract due to dehydration, a membrane permeation treatment of opening a hole having a size through which a probe can be introduced into a cell, a heat modification treatment of applying heat to cells, a treatment of hybridizing the target site and the probe, a washing treatment of removing unnecessary probes from the cells, and a treatment of staining the nucleus.

The measurement device 100 includes a flow cell 110, light sources 120 to 123, condenser lenses 130 to 133, dichroic mirrors 140 and 141, a condenser lens 150, an optical unit 151, a condenser lens 152, and an imaging unit 160. The sample 10 is flowed through a flow channel 111 of the flow cell 110.

The light sources 120 to 123 irradiate the sample 10 flowing through the flow cell 110 with light. The light sources 120 to 123 are constituted by, for example, semiconductor laser light sources. Light of wavelengths $\lambda 11$ to $\lambda 14$ is respectively emitted from the light sources 120 to 123.

The condenser lenses 130 to 133 respectively collect light of wavelengths $\lambda 11$ to $\lambda 14$ emitted from the light sources 120 to 123, respectively. The dichroic mirror 140 transmits light of wavelength $\lambda 11$ and refracts light of wavelength $\lambda 12$. The dichroic mirror 141 transmits light of wavelengths $\lambda 11$ and $\lambda 12$ and refracts light of wavelength $\lambda 13$. In this manner, the sample 10 flowing through the flow channel 111 of the flow cell 110 is irradiated with the light of wavelengths $\lambda 11$ to $\lambda 14$. The number of semiconductor laser light sources provided in the measurement device 100 is not limited as long as 1 or more light sources are provided. The number of semiconductor laser light sources can be selected from among, for example, 1, 2, 3, 4, 5 and 6.

When the sample 10 flowing through the flow cell 110 is irradiated with light of wavelengths $\lambda 11$ to $\lambda 13$, fluorescence is generated from the fluorescent dye staining the cells. Specifically, when the first fluorescent dye labeling the BCR locus is irradiated with the light of wavelength $\lambda 11$, first fluorescence of wavelength $\lambda 21$ is generated from the first fluorescent dye. When the second fluorescent dye labeling the ABL locus is irradiated with the light of wavelength $\lambda 12$, second fluorescence of wavelength $\lambda 22$ is generated from the second fluorescent dye. When the nuclear dye staining the nucleus is irradiated with the light of wavelength $\lambda 13$, third fluorescence of wavelength $\lambda 23$ is generated from the nuclear dye. When the sample 10 flowing through the flow cell 110 is irradiated with the light of wavelength $\lambda 14$, this light transmits through the cells. The transmitted light of wavelength $\lambda 14$ that has been transmitted through the cells is used for generating a bright field image. For example, in the embodiment, the first fluorescence is in a wavelength band of green light, the second fluorescence is in a wavelength band of red light, and the third fluorescence is in a wavelength band of blue light.

The condenser lens 150 collects the first to third fluorescence generated from the sample 10 flowing through the flow channel 111 of the flow cell 110 and the transmitted light transmitted through the sample 10 flowing through the flow channel 111 of the flow cell 110. The optical unit 151 has a configuration in which four dichroic mirrors are combined. The four dichroic mirrors of the optical unit 151 reflect the first to third fluorescence and the transmitted light at slightly different angles from each other and separate the light on a light receiving surface of the imaging unit 160. The condenser lens 152 condenses the first to third fluorescence and the transmitted light.

The imaging unit 160 is constituted by a time delay integration (TDI) camera. The imaging unit 160 images the first to third fluorescence and the transmitted light and outputs fluorescence images respectively corresponding to the first to third fluorescence and a bright field image corresponding to the transmitted light as imaging signals to the image processing device 200. The fluorescence images corresponding to the first to third fluorescence are hereinafter respectively referred to as a "first image", a "second image", and a "third image". The "first image", "second image" and "third image" preferably have the same size in order to analyze overlapping of bright spots. The "first image", "second image", and "third image" may be color images or gray scale images.

Figure 2A:
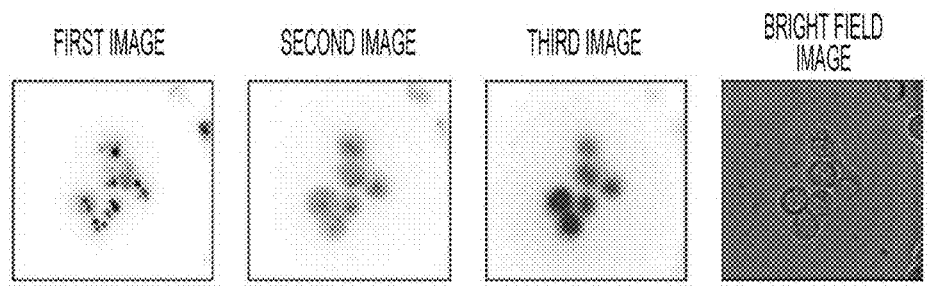
FIG. 2A is a diagram exemplifying first to third images and a bright field image acquired by the fluorescence image analyzing apparatus.

FIG. 2A shows examples of fluorescence images. In the first image of FIG. 2A, a portion that looks like a dark dot shows a bright spot of the first fluorescence, that is, a target site labeled with the first fluorescent dye. In the second image, although not as vivid as in the first image, a dark gray dot is observed in a light gray color indicating a nucleus. This indicates a bright spot of the second fluorescence, that is, a target site labeled with the second fluorescent dye. In the third image, a region of a substantially circular nucleus is represented in black. In a bright field image, the state of actual cells can be observed. Each image in FIG. 2A is an image showing an example in which white blood cells after a pretreatment are placed on a glass slide and observed under a microscope, and, in raw data of the fluorescence image, brighter spots indicate higher fluorescence intensity and darker spots indicate lower fluorescence intensity. In the first to third images in FIG. 2A, the gradation of the imaged raw data is reversed and represented in gray scale. In the case where the sample 10 flowing through the flow cell 110 is imaged by the imaging unit 160 as described above, since the cells flow through the flow channel 111 in a state of being separated from each other, the fluorescence image and the bright field image are acquired for each cell.

Returning to FIG. 1, the image processing device 200 includes a processing unit 11, a storage unit 12, a display unit 13, and an input unit 14 as a hardware configuration. The processing unit 11 is constituted by a processor (central processing unit: CPU). The storage unit 12 is constituted by a readable and writable memory (random access memory: RAM) used as a work area for various processes of the processing unit 11, a read-only memory (ROM) for storing computer programs and data, a hard disk, and the like. The processing unit 11 and the storage unit 12 can be configured by a general-purpose computer. The hard disk may be included in the computer or may be placed as an external device of the computer. The display unit 13 is constituted by a display. The input unit 14 is constituted by a mouse, a keyboard, a touch panel device, or the like. The processing unit 11 transmits data to and from the storage unit 12 via a bus 15, and inputs and outputs data to and from the display unit 13, the input unit 14, and the measurement device 100 via an interface 16.

The processing unit 11 reads out various computer programs stored in the ROM or the hard disk to the RAM, executes the computer programs, and thus processes the fluorescence image of cells obtained by the measurement of the sample 10 performed by the measurement device 100, and controls operations of the display unit 13, the input unit 14, and the like. Specifically, the processing unit 11 extracts a plurality of bright spots in a fluorescence image including a target site for each cell, and changes the pixel value of each of the plurality of extracted bright spots according to the pixel value of the bright spot.

A "pixel value" in this specification refers to a digital value assigned to each pixel of an image, and in particular, in an output image (so-called raw image) from a camera, refers to a value of the luminance of an imaging target object converted into a digital signal.

Hereinafter, an example of an image processing method of a fluorescence image performed by the processing unit 11 based on a computer program defining a processing procedure for processing a fluorescence image of a cell acquired by imaging the sample 10 will be described with reference to FIG. 3. The computer program is stored in the storage unit 12 in advance, but may be installed from a computer-readable portable recording medium (not shown) such as a CD-ROM, or, for example, may be installed by being downloaded from an external server via a network (not shown).

As shown in FIG. 3, the processing unit 11 performs respective processes at an image acquisition step S1, an extraction step S2 of a bright spot and a nucleus region, a bright spot emphasis step S3, a pixel value adjustment step S4, a pixel value changing step S5, an image combining step S6, and an image display step S7.

First, in step S1, the processing unit 11 acquires the first to third images displayed in grayscale by gradation inversion of the raw data captured by the imaging unit 160. The processing unit 11 causes the storage unit 12 to store the acquired first to third images.

Next, in step S2, the processing unit 11 extracts a bright spot (first bright spot) of first fluorescence in the first image, a bright spot (second bright spot) of second fluorescence in the second image, and a nucleus region in the third image.

Figure 2B:
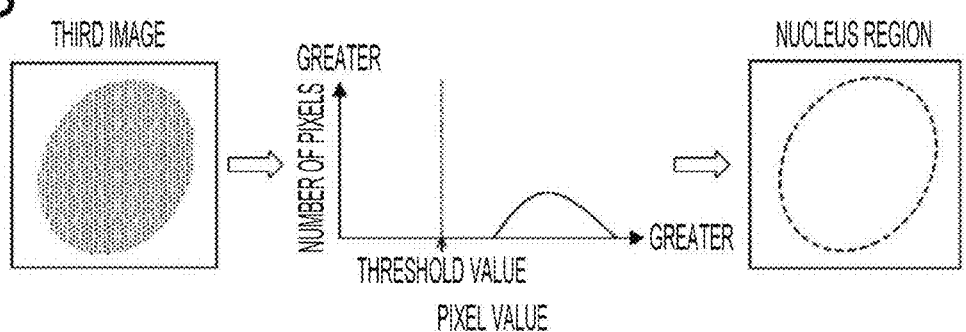
FIG. 2B is a schematic diagram for describing extraction of a nucleus region performed by the fluorescence image analyzing apparatus.
Figure 2C:
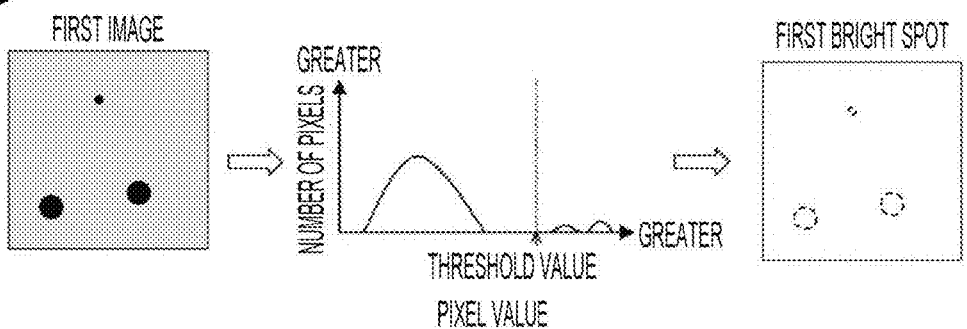
FIG. 2C and FIG. 2D are schematic diagrams for describing extraction of bright spots performed by the fluorescence image analyzing apparatus.
Figure 2D:
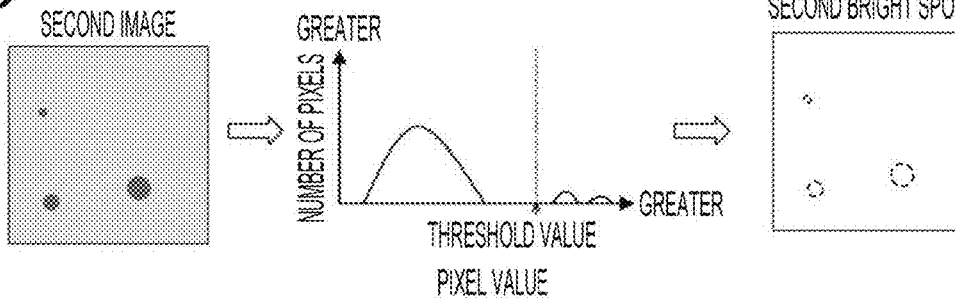

More specifically, referring to FIGS. 2B to 2D, the third image shown at the left end of FIG. 2B, the first image shown at the left end of FIG. 2C, and the second image shown at the left end of FIG. 2D are acquired from one cell flowing through the flow cell 110.

When a third image as shown at the left end of FIG. 2B is acquired, the processing unit 11 firstly generates a graph of pixel values and number of pixels based on the pixel value of each pixel in horizontal (x direction) m×vertical (y direction) n pixels constituting the third image as shown in the center of FIG. 2B. The "number of pixels" of the vertical axis indicates the number of pixels. The number of pixels of the image is not particularly limited, is, for example, horizontal 51×vertical 51. The spatial resolution per pixel is also not particularly limited. Then, the processing unit 11 sets a threshold value of the pixel value in the graph of FIG. 2B, and extracts a range where pixels having pixel values larger than the threshold value as a nucleus region as indicated by a broken line at the right end of FIG. 2B.

Next, when a first image as shown at the left end of FIG. 2C is acquired, the processing unit 11 firstly generates a graph of pixel values and number of pixels based on the pixel value of each pixel in horizontal (x direction) m×vertical (y direction) n pixels constituting the first image as shown in the center of FIG. 2C. Then, the processing unit 11 sets a threshold value of the pixel value in the graph of FIG. 2C, for example, as a boundary between a bright spot and the background based on an Otsu method, and extracts a range where pixels having pixel values larger than the threshold value as a first bright spot as indicated by a broken line at the right end of FIG. 2C. When extracting a first bright spot from the first image, an extremely small bright spot and an extremely large bright spot are excluded. The size of a bright spot can be represented by the area of the bright spot in the first image (the number of pixels included in the bright spot). The position of the nucleus region is compared with the position of the bright spot extracted from the first image, and a bright spot not included in the nucleus region is excluded. As a result, first bright spots are extracted from the first image, and the number and positions of the first bright spots are derived.

Next, when a second image as shown at the left end of FIG. 2D is acquired, the processing unit 11 generates a graph of pixel values and number of pixels based on the pixel value of each pixel in horizontal (x direction) m×vertical (y direction) n pixels constituting the second image as shown in the center of FIG. 2D, similarly to the case of the first image. Then, the processing unit 11 sets a threshold value of the pixel value in the graph of FIG. 2D, and extracts a range where pixels having pixel values larger than the threshold value as a second bright spot as indicated by a broken line at the right end of FIG. 2D. When extracting a second bright spot from the second image, an extremely small bright spot and an extremely large bright spots are excluded. The size of a bright spot can be represented by the area of the bright spot in the second image (the number of pixels included in the bright spot). The position of the nucleus region is compared with the position of the bright spot extracted from the second image, and a bright spot not included in the nucleus region is excluded. As a result, second bright spots are extracted from the second image, and the number and positions of the second bright spots are derived.

The positions of the nucleus region and the bright spots in each image can be measured by, for example, determining coordinate information (x, y) for horizontal (x direction) m×vertical (y direction) n pixels constituting each image and based on the coordinate information of a plurality of pixels included in the nucleus region and bright spots.

The processing unit 11 may extract a first bright spot, a second bright spot, and a nucleus region respectively from the first image, the second image, and the third image by calculation according to the above procedure without generating the graphs as shown in the center of FIGS. 2B to 2D. The extraction of the bright spots may be performed by determining the degree of matching between a distribution waveform of normal bright spots and a target region of determination and extracting the target region of determination as a bright spot when the degree of matching is high. Although the processing unit 11 detects cells by extracting the nucleus region from the third image in the description above, the processing unit 11 may detect the cells based on a bright field image. In the case where cells are detected based on the bright field image, acquisition of the third image may be omitted. A bright spot in the present embodiment refers to a point of small fluorescence generated in the fluorescence image. More specifically, the bright spot refers to the central point of a bright spot (the position of the pixel having the greatest pixel value (fluorescence intensity)). The extraction of the bright spots can be performed by, for example, converting the color gradation of pixels other than the pixels designated as bright spots to the same level as the background.

Returning to FIG. 3, next, in step S3, the processing unit 11 emphasizes bright spots by relatively increasing the pixel values of the extracted plurality of first bright spots and second bright spots respectively for the first image and the second image with respect to the other region (background) than the bright spots.

First, a method of determining whether or not a cell is an abnormal cell will be described.

Figure 4A:
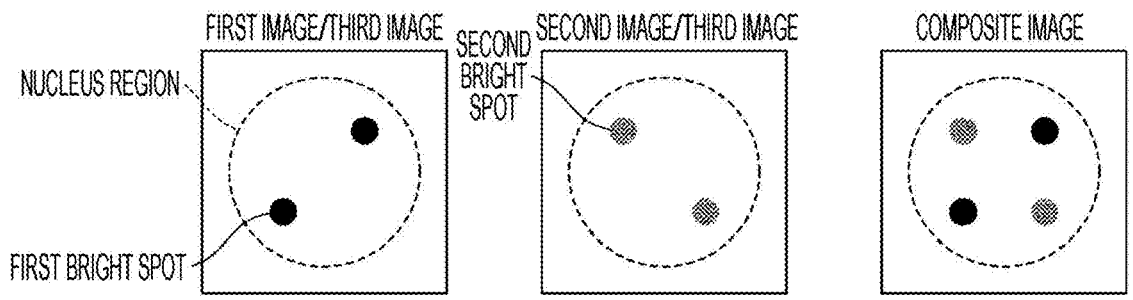
FIGS. 4A to 4D are respectively schematic diagrams for describing information of bright spots of a negative pattern and positive patterns 1 to 3.
Figure 4B:
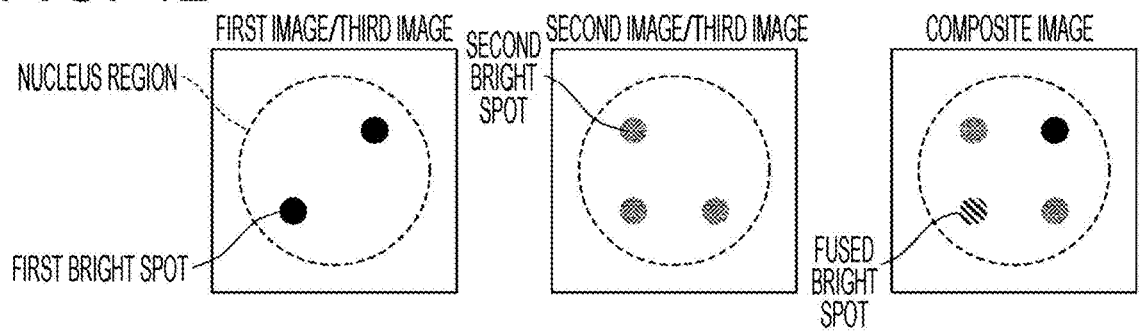
Figure 4C:
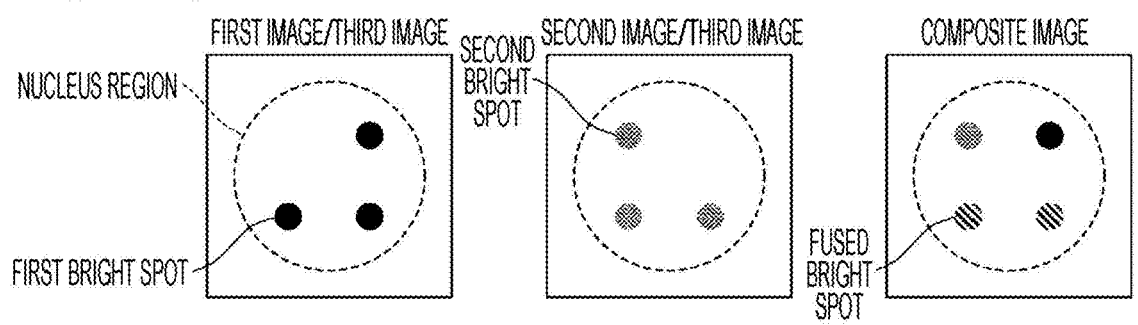
Figure 4D:
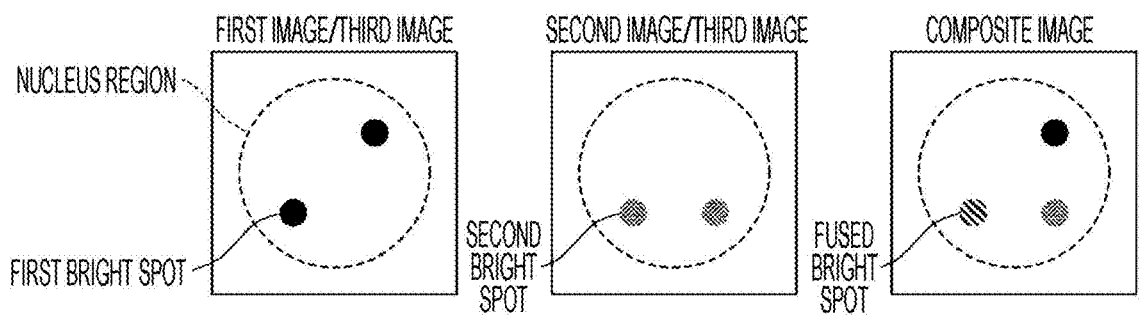

FIG. 4A shows an arrangement example of bright spots of a normal cell having no chromosomal abnormality, that is, an example of bright spot pattern (negative pattern), and FIGS. 4B to 4D show examples of bright spot patterns (positive patterns) of abnormal cells. In any of FIGS. 4A to 4D, each image is shown in a state of being superimposed with the third image.

As shown in FIG. 4A, when there is no chromosomal abnormality such as translocation of BCR locus and ABL locus, each gene exists as one pair in one nucleus, and each allele independently exists. Therefore, in the first image, there are two first bright spots in one nucleus region. In the second image, there are two second bright spots in one nucleus region. In this case, if the first image and the second image imaged at the same size are superimposed and combined, in the composite image, the two first bright spots and the two second bright spots are present without overlapping in one nucleus region. Therefore, a cell in which two first bright spots and two second bright spots are present in the nucleus region as shown in FIG. 4A is determined to be a normal cell in which no chromosomal abnormality is observed, that is, the chromosome abnormality is negative.

In contrast, as shown in FIG. 4B, when a part of the ABL locus has moved to chromosome 9 due to translocation, there are two first bright spots in the nucleus in the first image, and there are three second bright spots in the nucleus in the second image. In this case, when combining the first image and the second image, in the composite image, one first bright spot, two second bright spots, and a bright spot (fused bright spot) of fourth fluorescence (yellow in the present embodiment) in which a first bright spot and a second bright spot overlap each other are present in one nucleus. Therefore, as shown in FIG. 4B, a cell in which the respective bright spots are present is determined to be an abnormal cell in which translocation occurs in the BCR locus and the ABL locus, that is, chromosomal abnormality is positive.

As shown in FIG. 4C, when a part of the BCR locus has moved to chromosome 22 due to translocation and a part of the ABL locus has moved to the chromosome 9, there are three first bright spots in the nucleus in the first image, and there are three second bright spots in the nucleus in the second image. In this case, when combining the first image and the second image, in the composite image, one first bright spot, one second bright spots, and two fused bright spots in which first bright spots and second bright spots overlap each other are present in one nucleus. Therefore, as shown in FIG. 4C, a cell in which the respective bright spots are present is determined to be an abnormal cell in which translocation occurs in the BCR locus and the ABL locus, that is, chromosomal abnormality is positive.

As shown in FIG. 4D, when a part of the ABL locus has moved to chromosome 9 due to translocation, there are two first bright spots in the nucleus in the first image, and there are two second bright spots in the nucleus in the second image. In this case, when combining the first image and the second image, in the composite image, one first bright spot, one second bright spots, and one fused bright spot in which a first bright spot and a second bright spot overlap each other are present in one nucleus. Therefore, as shown in FIG. 4D, a cell in which the respective bright spots are present is determined to be an abnormal cell in which translocation occurs in the BCR locus and the ABL locus, that is, chromosomal abnormality is positive.

In this manner, it is possible to determine whether or not each cell is an abnormal cell having a chromosomal abnormality based on the positions and the number of the respective bright spots in the composite image obtained by combining the first image and the second image. The first bright spot, the second bright spot, and the fused bright spot can be indicated by color information in each image and composite image thereof such that the operator or the like can easily recognize the first bright spot, the second bright spot, and the fused bright spot by seeing the display unit 13. That is, instead of displaying each image in gray scale, the color of each pixel of the first image can be displayed in green color gradation (RGB value) of the first fluorescence based on the pixel value, and thus a region bright in green (first fluorescence) can be recognized as a first bright spot. In the second image, the color of each pixel can be displayed in red color gradation (RGB value) of the second fluorescence based on the pixel value, and thus a region bright in red (second fluorescence) can be recognized as a second bright spot. In a composite image in which the first image and the second image are superimposed, when there is a fused bright spot in which a first bright spot that is green (first fluorescence) and a second bright spot that is red (second fluorescence, a region bright in yellow (fourth fluorescence) can be recognized as a fused bright spot based on the combination of the RGB values of pixels of the fused bright spot. Therefore, when the cell is an abnormal cell, a first bright spot that is green (first fluorescence), a second bright spot that is red (second fluorescence), a fused bright spot that is yellow (fourth fluorescence) are present in the nucleus region.

Figure 5A:
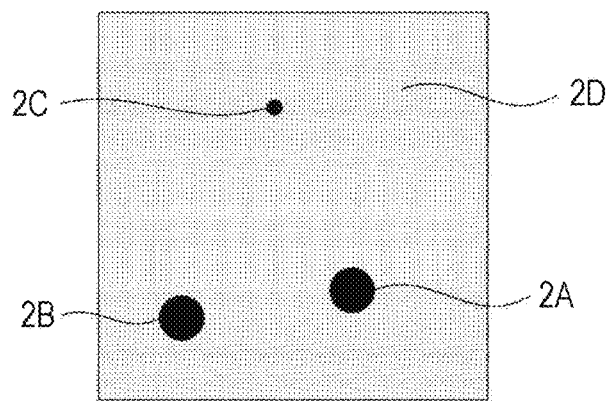
FIG. 5A is a schematic diagram of a first image after an extraction process of first bright spots.
Figure 6A:
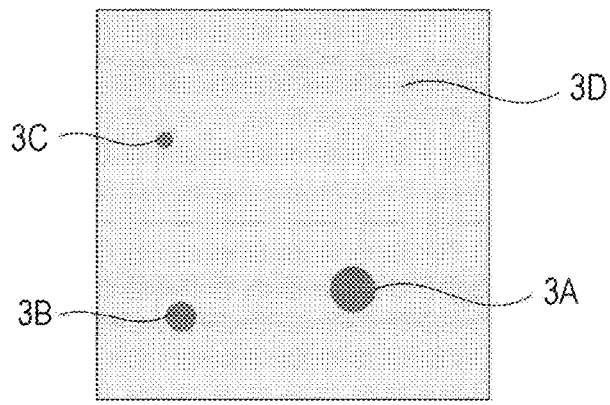
FIG. 6A is a schematic diagram of a second image after an extraction process of second bright spots.

As shown in FIGS. 5A and 6A, respective bright spots extracted from the first image and the second image include a light bright spot and a dark bright spot. For example, in FIG. 5A, three first bright spots 2A to 2C are present in the first image. While the two first bright spots 2A and 2B are light, the one first bright spot 2C is dark. Meanwhile, in FIG. 6A, three second bright spots 3A to 3C are present in the second image. While the one second bright spot 3A is light, the two second bright spots 3B and 3C are dark. The lightness and darkness of a bright spot are indicated by the size (area) of the bright spot in FIGS. 5A and 6A. As shown in FIGS. 5A and 6A, the dark bright spots 2B, 2C and 3C have a small difference in brightness from backgrounds 2D and 3D in respective images, the dark bright spots 2B, 2C, and 3C are difficult for the operator or the like to visually recognize, and thus the operator or the like tends to miss the dark bright spots 2B, 2C, and 3C. Therefore, the processing unit 11 performs a bright spot emphasis process to clarify the dark bright spots 2B, 2C, and 3C of weak fluorescence in the first image and the second image to make it easier to recognize dark bright spots in each image.

Figure 5B:
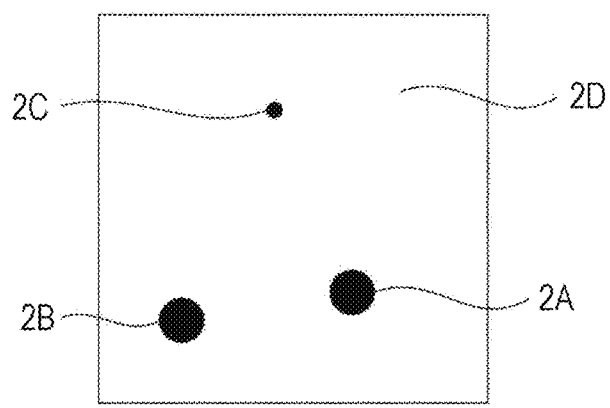
FIG. 5B is a schematic diagram of the first image after an emphasis process of the first bright spots.
Figure 6B:
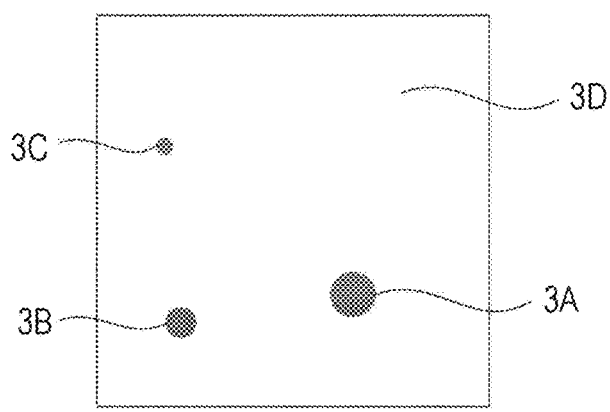
FIG. 6B is a schematic diagram of the second image after an emphasis process of the second bright spots.

In the bright spot emphasis process, for example, as shown in FIGS. 5B and 6B, the pixel values of the first bright spots 2A to 2C and the second bright spots 3A to 3C can be relatively increased with respect to the pixel values of the backgrounds 2D and 3D by decreasing the pixel values of pixels positioned in the backgrounds 2D and 3D of the first image and the second image to predetermined pixel values. The pixel values of the first bright spots 2A to 2C and the second bright spots 3A to 3C can be relatively increased with respect to the pixel values of the backgrounds 2D and 3D by increasing the pixel values of pixels positioned in the first bright spots 2A to 2C and the second bright spots 3A to 3C by multiplying the pixel values by predetermined coefficients. Further, the pixel values of the first bright spots 2A to 2C and the second bright spots 3A to 3C can be relatively increased with respect to the pixel values of the backgrounds 2D and 3D by increasing the pixel values of pixels of the first image and the second image by multiplying the pixels positioned in the first bright spots 2A to 2C and the second bright spots 3A to 3C by larger coefficients or decreasing the pixel values of pixels positioned in the backgrounds 2D and 3D by multiplying the pixels positioned in the backgrounds 2D and 3D by smaller coefficients.

The processing unit 11 causes the storage unit 12 to store the first image and the second image in which a first bright spot and a second bright spot have been emphasized in the bright spot emphasis process.

Returning to FIG. 3, next, in step S4, the processing unit 11 adjusts the pixel values of a bright spot extracted from one of the first image and the second image based on pixel values of a bright spot extracted from the other of the first image and the second image. Specifically, when there is a difference between the pixel values of the first bright spot of the first image and the pixel values of the second bright spot of the second image, the highest values of the pixel values of both bright spots are caused to match. For example, the highest values of the pixel values of both bright spots can be caused to match by increasing the pixel values of pixels positioned in a bright spot of one image whose highest value of pixel values is lower by, for example, multiplying the pixel values by a predetermined coefficient. The highest values of the pixel values of both bright spots can be caused to match by increasing the pixel values of pixels positioned in a bright spot of the image whose highest value of pixel values is lower by, for example, multiplying the pixel values by a predetermined first coefficient and increasing the pixel values of pixels positioned in a bright spot of the image whose highest value of pixel values is higher by, for example, multiplying the pixel values by a predetermined second coefficient smaller than the first coefficient.

In the case where there is a large difference between the pixel values of a first bright spot of green (first fluorescence) and the pixel values of a second bright spot of red (second fluorescence) at a fused bright spot where the first bright spot and the second bright spot are fused, the fused bright spot may not be displayed yellow (fourth fluorescence). For example, if the pixel values of the first bright spot of green (first fluorescence) is significantly larger than the pixel value of the second bright spot of red (second fluorescence), the color of the fused bright spot becomes close to green (first fluorescence) and becomes less likely to appear yellow (fourth fluorescence). In this case, even if the operator or the like visually recognizes the fused bright spot, the operator or the like does not recognize the spot as a fused bright spot but mistakenly recognizes the spot as a first bright spot. Therefore, the processing unit 11 corrects the pixel values of the first bright spot of the first image and the pixel values of the second bright spot of the second image to the same level by the adjustment process of the pixel values to cause the fused bright spot in which the first bright spot of green (first fluorescence) and the second bright spot of red (second fluorescence) are fused is displayed yellow (fourth fluorescence) such that it is easier to recognize the fused bright spot.

The processing unit 11 causes the storage unit 12 to store the first image and the second image in which pixel values of a first bright spot and a second bright spot have been adjusted in the adjustment process of pixel values.

Returning to FIG. 3, next, in step S5, the processing unit 11 changes, according to the pixel values of each bright spot, the pixel values of a plurality of first bright spots and a plurality of second bright spots respectively extracted from the first image and the second image.

As shown in FIG. 5A and FIG. 6A, among the bright spots 2A to 2C and 3A to 3C extracted from the first image and the second image, the dark bright spots 2B, 2C, and 3C are difficult for an observer to visually recognize in the respective images, and are likely to be missed by the observer. As shown in FIGS. 5B and 6B, the dark bright spots 2B, 2C, and 3C are harder for the observer to visually recognize than the light bright spots 2A, 2B, 3A, and 3B in the respective images even after the each image after the bright spot emphasis process. Besides, in the case where there is large difference between the pixel values of the dark bright spots 2B, 2C, and 3C and the light bright spots 2A, 3A, and 3B, and, for example, the bright spot 3B of dark red (second fluorescence) of the second image overlaps with the bright spot 2B of light green (first fluorescence) of the first image to form a fused bright spot when combining the first image and the second image, the color of the fused bright spot 4B becomes close to the green (first fluorescence) of the light first bright spot and becomes less likely to appear yellow. For this reason, an operator or the like is likely not to recognize the spot as a fused bright spot and mistakenly recognize the spot as another bright spot.

Figure 5C:
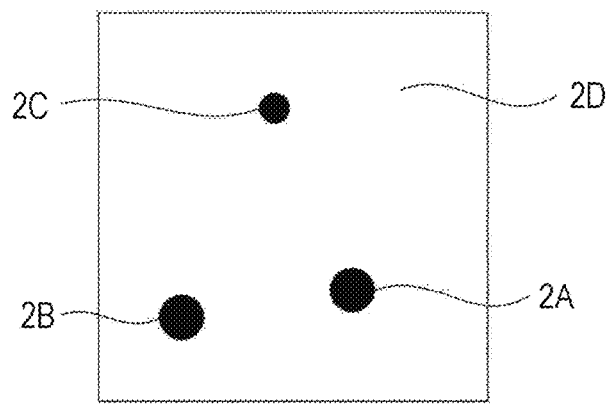
FIG. 5C is a schematic diagram of the first image after a process of changing the pixel values of the first bright spots.
Figure 6C:
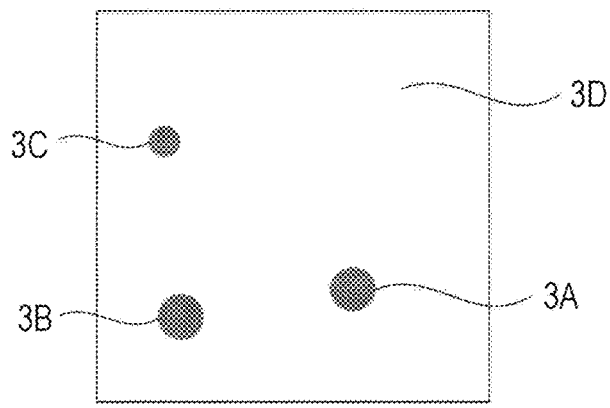
FIG. 6C is a schematic diagram of the second image after a process of changing the pixel values of the second bright spots.
Figure 7A:
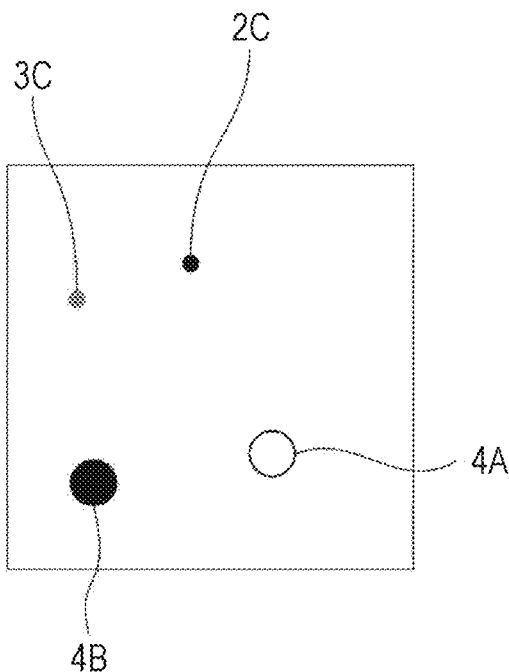
FIG. 7A is a schematic diagram of a composite image of the first image after the emphasis process of the first bright spots and the second image after the emphasis process of the second bright spots.
Figure 7B:
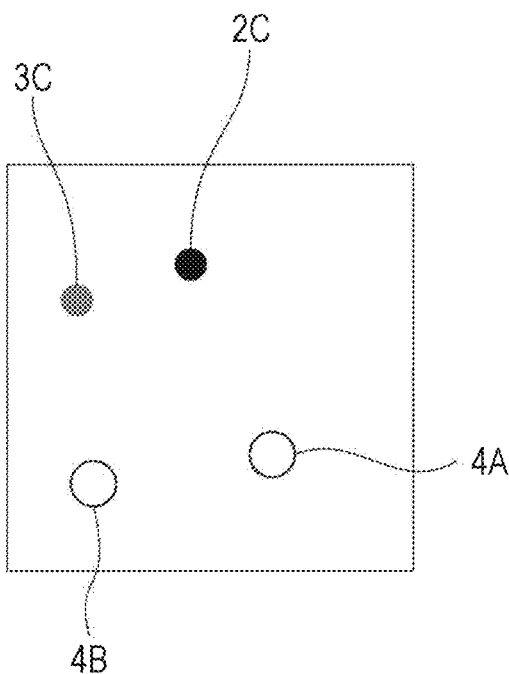
FIG. 7B is a schematic diagram of a composite image of the first image after the process of changing the pixel values of the first bright spots and the second image after the process of changing the pixel values of the second bright spots.
Figure 8A:
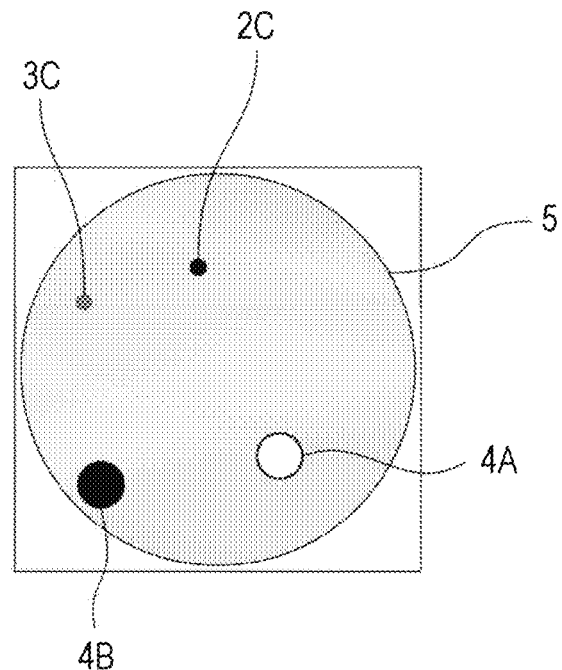
FIG. 8A is a schematic diagram of a composite image in which a third image is combined with the composite image of the first image and the second image of FIG. 7A.
Figure 8B:
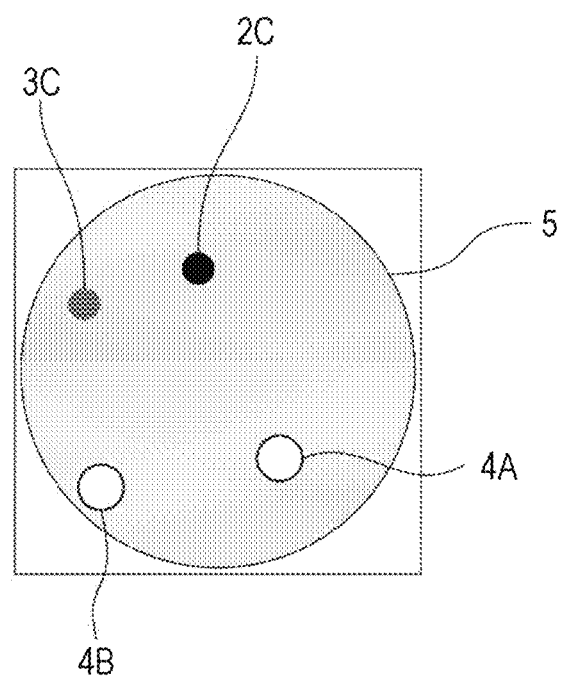
FIG. 8B is a schematic diagram of a composite image in which the third image is combined with the composite image of the first image and the second image of FIG. 7B.

Therefore, the processing unit 11 changes the pixel values of a plurality of bright spots having different pixel values at different change rates in each of the first image and the second image by the process of changing the pixel values. The change rates include increase rates and decrease rates. For example, as shown in FIGS. 5C and 6C, the pixel value of a pixel having a smaller pixel value is increased with a higher increase rate. As a result, regarding the dark bright spots 2C, 3B, and 3C having small pixel values, the pixel values thereof are increased more greatly than the light bright spots 2A, 2B, 3A, and 3B having large pixel values so as to brighten the dark bright spots 2C, 3B, and 3C to facilitate recognizing the dark bright spots 2C, 3B, and 3C. FIG. 8 shows a composite image in which the first image, the second image, and the third image are combined. As can be seen by comparing FIG. 8A with FIG. 8B, the dark bright spots 2C, 3B, and 3C having small pixel values are made easier to recognize without being buried in the nucleus region 5 of the back ground in the case where the bright spots 2A to 2C and 3A to 3C of the first image and the second image are superimposed on the nucleus region 5 of the third image. Besides, as can be seen from the comparison between FIG. 7B and FIG. 8B and the comparison between FIG. 7A and FIG. 8A, the processing unit 11 reduces the difference in pixel value between the dark bright spots 2C, 3B, and 3C and the light bright spots 2A, 2B, and 3A having large pixel values such that the fused bright spot 4B in which the first bright spot 2B of green (first fluorescence) and the second bright spot 3B of red (second fluorescence) are fused is displayed in a color closer to yellow (fourth fluorescence) and that it is easier to recognize the fused bright spot 4B when the first image and the second image are combined.

In the process of changing pixel values, the pixel values may be changed in any method as long as the method follows a rule that the pixel values of pixels included in each bright spot in each image is increased by using a larger increase rate for a pixel having a smaller pixel value, and the method of changing the pixel values is not particularly limited. In the process of changing pixel values, it is preferable to increase the pixel values by using a larger increase rate for a pixel having a smaller pixel value while maintaining the magnitude relationship between the pixel values of respective pixels included in each bright spot. It is preferable to maintain the pixel value of a pixel having the highest pixel value among the pixels whose pixel values are to be changed and which are included in each bright spot. This makes it possible to reproduce the original brightness relationship between the bright spots in each image after the changing process.

Figure 9A:
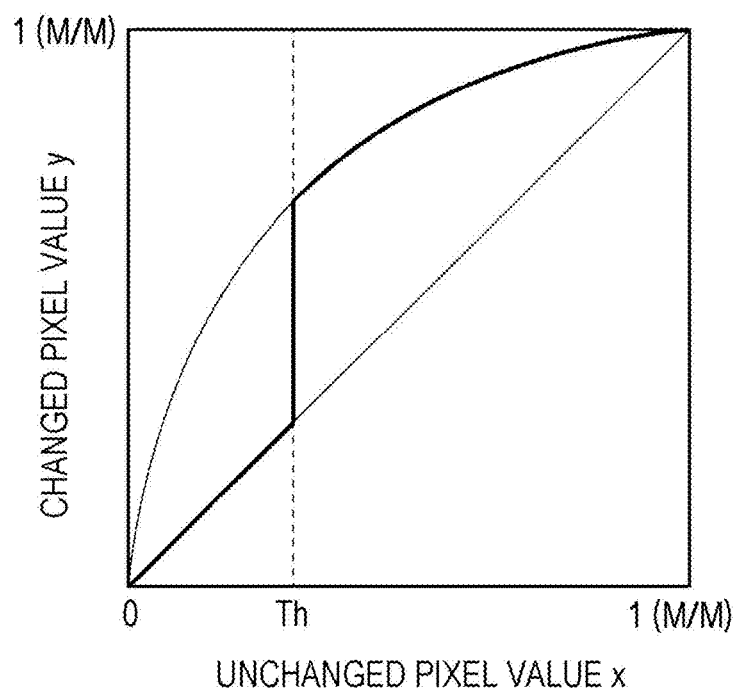
FIGS. 9A and 9B are diagrams for describing an example of a functional expression in the process of changing pixel values.

As the process of changing pixel values, for example, as shown in FIG. 9A, it is possible to change an unchanged pixel value x to a changed pixel value y by Expression 1 below for each pixel included in an image to be changed. In Expression 1 and FIG. 9A, both the highest pixel values of the unchanged pixel value x and the changed pixel value y are a highest pixel value M of a pixel before being changed, and a range of pixel values 0 to M is normalized by the highest pixel value M. According to Expression 1 and FIG. 9A, for a pixel whose unchanged pixel value x is smaller than a threshold value Th, the changed pixel value y becomes equal to the unchanged pixel value x, and thus the pixel value is maintained without being changed. In contrast, for a pixel whose unchanged pixel value x is larger than the threshold value Th, the pixel value of a pixel having a smaller pixel value is increased with a larger increase rate by a predetermined functional formula while maintaining the magnitude relationship between pixel values. By setting the threshold value Th to the lowest pixel value of pixel values of pixels included in each bright spot, just the pixel values of each bright spot can be changed according to the pixel values thereof.

$$y=x^\gamma (\text{where } x \geq Th \text{ and } \gamma<1) \text{ and } y=x(\text{where } x<Th) \quad [\text{Expression 1}]$$

Figure 9B:
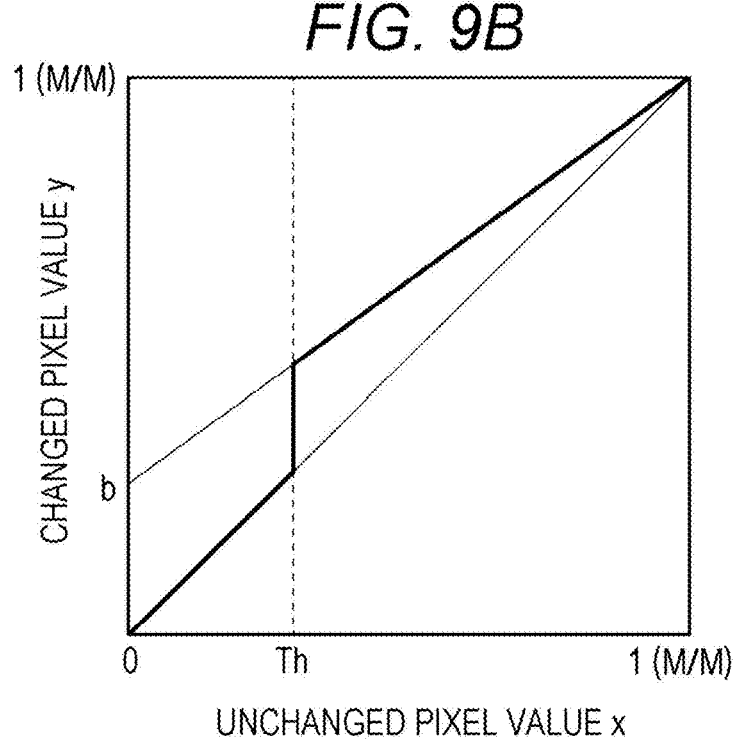

In another example of the process of changing pixel values, as shown in FIG. 9B, it is possible to change the unchanged pixel value x to the changed pixel value y by Expression 2 below for each pixel included in the image to be changed. Also in Expression 2 below and FIG. 9B, both the highest pixel values of the unchanged pixel value x and the changed pixel value y are the highest pixel value M of a pixel before being changed, and the range of pixel values 0 to M is normalized by the highest pixel value M. Also according to Expression 2 and FIG. 9B, for a pixel whose unchanged pixel value x is smaller than the threshold value Th, the changed pixel value y becomes equal to the unchanged pixel value x, and thus the pixel value is maintained without being changed. In contrast, for a pixel whose unchanged pixel value x is larger than the threshold value Th, the pixel value of a pixel having a smaller pixel value is increased with a larger increase rate by a predetermined functional formula while maintaining the magnitude relationship between pixel values. By setting the threshold value Th to the lowest pixel value of pixel values of pixels included in each bright spot, just the pixel values of each bright spot can be changed according to the pixel values thereof.

$$y=(1-b)x+b(\text{where } x \geq Th), \text{ and } y=x(\text{where } x<Th) \quad [\text{Expression 2}]$$

In the process of changing pixel values, the pixel values may be changed by a reference process using a predetermined look up table following the rule described above instead of arithmetic processing using a functional expression.

The processing unit 11 causes the storage unit 12 to store the first image and the second image in which pixel values of a first bright spot and a second bright spot have been changed in the process of changing pixel values.

Returning to FIG. 3, next, in step S6, the processing unit 11 combines the first image and the second image, from which the bright spots described above have been extracted and which have been subjected to the image processing, and the third image from which the nucleus region has been extracted. The processing unit 11 is capable of generating, by image combination, a plurality of kinds of composite images such as a composite image of the first image and the third image, a composite image of the second image and the third image, a composite image of the first image and the second image, and a composite image of the first image, the second image, and the third image. It is not always necessary to create all of the above-described plurality of kinds of composite images. The processing unit 11 causes the storage unit 12 to store each composite image that has been generated.

Finally, in step S7, the processing unit 11 displays the first image and the second image, from which the bright spots described above have been extracted and which have been subjected to the image processing, the third image from which the nucleus region has been extracted, and further each composite image generated by image combination on the display unit 13. The processing unit 11 does not necessarily display all of the above-described images on the display unit 13, and can displaying only necessary images selected by the operator or the like on the display unit 13.

The operator or the like observes each image displayed on the display unit 13 and checks whether or not each cell is an abnormal cell based on the color and number of bright spots in each image.

According to the present disclosure, when the operator or the like observes a fluorescence image of a cell displayed on the display unit 13, first, pixel values of pixels in each bright spot is relatively enhanced with respect to pixel values of pixels in the background outside the bright spot by the bright spot emphasis process in the first image and the second image from which bright spots have been extracted. Therefore, even if dark bright spots having low pixel values are extracted from each image, it is easier for the operator or the like to visually recognize the dark bright spots. In the first image and the second image, dark bright spots having low pixel values are enhanced by the process of changing pixel values such that the difference between the pixel values of the dark bright spots and the pixel values of light bright spots having high pixel values is reduced, and thus it is further easier for the operator or the like to visually recognize the dark bright spots. In addition, since dark bright spots having low pixel values are enhanced by the process of changing pixel values such that the difference between the pixel values of the dark bright spots and the pixel values of light bright spots having high pixel values is reduced in the first image and the second image, a first bright spot and a second bright spot are superimposed in a fused bright spot in a composite image of the first image and the second image in a state in which the difference between pixel values thereof is reduced. Accordingly, the fused bright spot is displayed in yellow of fourth fluorescence or a color close to yellow, and thus it is easier for the operator or the like to detect the fused bright spot by visual observation. The fused bright spot in the composite image of the first image and the second image can be displayed yellow of fourth fluorescence by the adjustment process of pixel values between the first bright spot of the first image and the second bright spot of the second image, and thus it is further easier for the operator or the like to detect the fused bright point by visual observation.

As described above, according to the present disclosure, even in the case where a light bright spot having high pixel values and a dark bright spot having low pixel values are present in one fluorescence image, confirmation of a bright spot in image observation and detection of a fused bright spot in analysis of a composite image of two fluorescence images can be performed easily. Therefore, it is possible to easily and highly accurately determine whether each cell is a normal cell or an abnormal cell.

Although one embodiment of the present disclosure has been described above, the present disclosure is not limited to the present embodiment described above, and various modifications are possible without departing from the gist of the present disclosure.

For example, in the present embodiment described above, the processing unit 11 increases the pixel values of each bright spot in each fluorescence image (first image and second image) by using a larger increase rate for a pixel having a smaller pixel value in the process of changing the pixel values in step S5 of FIG. 3. Thus, the difference between the pixel values of a dark bright spot and a light bright spot in each fluorescence image is reduced. However, the method of the process of changing pixel values is not limited to this. For example, the difference between the pixel values of a dark bright spot and a light bright spot in each fluorescence image can be reduced by decreasing the pixel value of a pixel having a larger pixel value with a larger decrease rate in each bright spot in each fluorescence image.

In the present embodiment described above, regarding each fluorescence image (first image and second image) captured by the imaging unit 160, the processing unit 11 displays, on the display unit 13, fluorescence images after image processing. However, among fluorescence images before and after the image processing, any fluorescence image selected by the input unit 14 may be displayed on the display unit 13. That is, the first image, the second image, and the third image before the image processing by the processing unit 11, and a composite image in which at least two of these are combined may be displayed on the display unit 13.

The processing unit 11 performs, in the processing procedure of processing a fluorescence image of FIG. 3, the adjustment process of pixel values of bright spots between a plurality of fluorescence images in step S4 and the process of changing pixel values of a plurality of bright spots in each fluorescence image in step S5. However, the adjustment process of pixel values of step S4 may be performed after the process of changing pixel values of step S5. The processing unit 11 does not need to perform and may omit the adjustment process of pixel values of step S4.

The processing unit 11 performs, in the processing procedure of processing a fluorescence image of FIG. 3, the extraction process of a bright spot from a fluorescence image in step S2, and then the bright spot emphasis process in the fluorescence image in step S3. However, the bright spot emphasis process of step S3 may be performed after the adjustment process of pixel values of step S4 or after the process of changing pixel values of step S5. The processing unit 11 does not need to perform and may omit the bright spot emphasis process of step S3.

Figure 10:
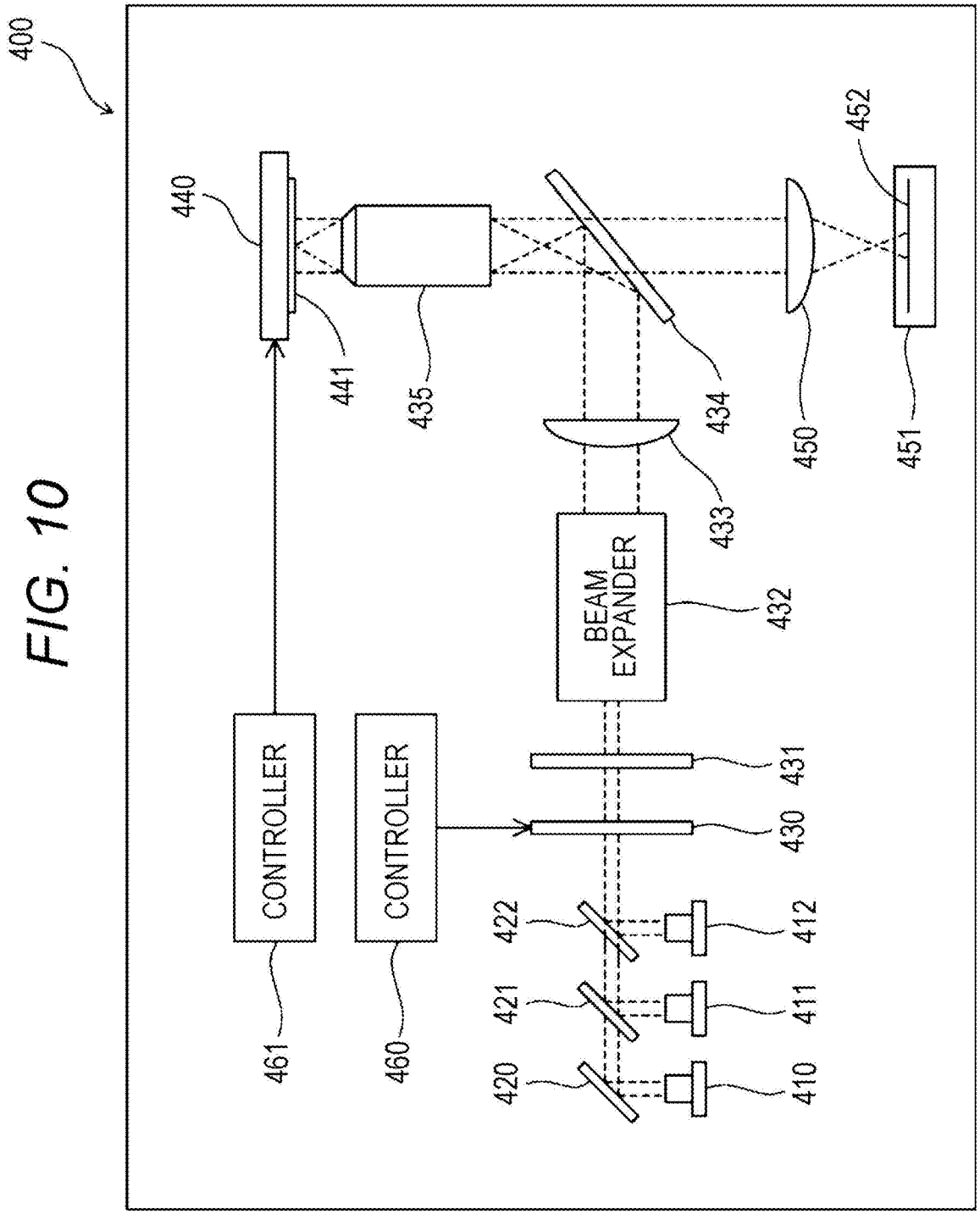
FIG. 10 is a schematic diagram showing a configuration of another example of a measurement device.

In the above-described fluorescence image analyzing apparatus 1 of the present embodiment, the measurement device 100 shown in FIG. 1 may be replaced by a measurement device 400 including a fluorescence microscope shown in FIG. 10.

The measurement device 400 shown in FIG. 10 includes light sources 410 to 412, a mirror 420, dichroic mirrors 421 and 422, a shutter 430, a quarter-wave plate 431, a beam expander 432, a condenser lens 433, a dichroic mirror 434, an objective lens 435, a stage 440, a condenser lens 450, an imaging unit 451, and controllers 460 and 461. On the stage 440, a glass slide 441 is installed. On the glass slide 441, the sample 10 (shown in FIG. 1) prepared by the pretreatment in the pretreatment device 300 is placed.

The light sources 410 to 412 are respectively similar to the light sources 120 to 122 shown in FIG. 1. The mirror 420 reflects light from the light source 410. The dichroic mirror 421 transmits light from the light source 410 and reflects light from the light source 411. The dichroic mirror 422 transmits light from the light sources 410 and 411 and reflects light from the light source 412. The optical axes of the light from the light sources 410 to 412 are matched with each other by the mirror 420 and the dichroic mirrors 421 and 422.

The shutter 430 is driven by the controller 460 to switch between a state of transmitting light emitted from the light sources 410 to 412 and a state of blocking light emitted from the light sources 410 to 412. As a result of this, the irradiation time of the sample 10 with light is adjusted. The quarter-wave plate 431 converts linearly polarized light emitted from the light sources 410 to 412 into circularly polarized light. Fluorescent dye bound to a probe reacts to light of a predetermined polarization direction. Therefore, by converting excitation light emitted from the light sources 410 to 412 into circularly polarized light, the polarization direction of the excitation light becomes more likely to match the polarization direction to which the fluorescent dye reacts. This makes it possible to efficiently excite fluorescence in the fluorescent dye. The beam expander 432 expands a light irradiation area on the glass slide 441. The condenser lens 433 collects light so that the glass slide 441 is irradiated with parallel light from the objective lens 435.

The dichroic mirror 434 reflects light emitted from the light sources 410 to 412, and transmits fluorescence generated from the sample 10. The objective lens 435 guides the light reflected by the dichroic mirror 434 to the glass slide 441. The stage 440 is driven by the controller 461. The fluorescence generated from the sample 10 passes through the objective lens 435 and passes through the dichroic mirror 434. The condenser lens 450 collects the fluorescence transmitted through the dichroic mirror 434 and guides the light to an imaging surface 452 of the imaging unit 451. The imaging unit 451 captures an image of the fluorescence radiated on the imaging surface 452, and generates a fluorescence image. The imaging unit 451 is constituted by, for example, a charge coupled device (CCD).

The controllers 460 and 461 and the imaging unit 451 are connected to the processing unit 11 shown in FIG. 1, and the processing unit 11 controls the controllers 460 and 461 and the imaging unit 451 and receives the fluorescence image captured by the imaging unit 451. Unlike the case where the flow cell 110 is used as shown in FIG. 1, the fluorescence image captured by the imaging unit 451 may be in a state in which cells are in close contact with each other as shown in FIG. 2A. Therefore, the processing unit 11 performs a process of dividing the acquired fluorescence image for each nucleus of a cell, a process of setting a region corresponding to one nucleus of a cell in the fluorescence image, or the like.

Also in the measurement device 400 shown in FIG. 10, three fluorescence images (first image to third image) can be acquired as in the present embodiment. Therefore, by generating a composite image by image processing of the fluorescence images, the operator or the like can easily and highly accurately determine whether each cell is a normal cell or an abnormal cell.

In the fluorescence image analyzing apparatus 1 of the present embodiment described above, the processing unit 11 may be connected to the pretreatment device 300 via the interface 16 so that data can be inputted and outputted therebetween.

A storage medium storing a computer program defining a processing procedure for processing the fluorescence images of cells by the processing unit 11 of the image processing device 200 described above can also be provided.

In the fluorescence image analyzing apparatus 1 of the present embodiment described above, a BCR/ABL fusion gene. In addition to the BCR/ABL fusion gene, examples of chromosomal translocations for which a fused bright spot can be detected by the FISH method include AML1/ETO (MTG8) fusion gene (t(8;21)), PML/RARα fusion gene (t(15;17)), AML1 (21q22) translocation, MLL (11q23) translocation, TEL (12p13) translocation, TEL/AML1 fusion gene (t(12;21)), IgH (14q32) translocation, CCND1 (BCL1)/IgH fusion gene (t(11;14)), BCL2 (18q21) translocation, IgH/MAF fusion gene (t(14;16)), IgH/BCL2 fusion gene (t(14;18)), c-myc/IgH fusion gene (t(8;14)), FGFR3/IgH fusion gene (t(4;14)), BCL6 (3q27) translocation, c-myc (8q24) translocation, MALT1 (18q21) translocation, API2/MALT1 fusion gene (t(11;18) translocation), TCF3/PBX1 fusion gene (t(1;19) translocation), EWSR1 (22q12) translocation, and PDGFRβ (5q32) translocation.

Another exemplary embodiment can be applied to chromosomal abnormality of the ALK locus. In a positive pattern, since the ALK gene is cleaved, only one fused bright spot is recognized (in the case where only one of the alleles is cleaved) or no fused bright spot is recognized (in the case where both of the alleles are cleaved). The negative pattern and the positive pattern are the same for the ROS1 gene and the RET gene in addition to the ALK gene.

Another exemplary embodiment can be applied to chromosomal abnormality of deletion of the long arm of chromosome 5 (5q). For example, the first fluorescently labeled probe is designed to bind to the long arm of chromosome 5, and the second fluorescently labeled probe is designed to bind to the centromere of chromosome 5. In the negative pattern, since the number of centromere of chromosome 5 is the same as the number of long arm of chromosome 5, the number of bright spots (first bright spots) of the first fluorescently labeled probe and bright spots (second bright spots) of the second fluorescently labeled probe are each two, reflecting the number of homologous chromosomes. In the positive pattern, long arm deletion occurs in one or both of chromosome 5 and the number of the first bright spots is only one or zero. This negative pattern and positive pattern are the same for deletion of short arm or long arm of other chromosomes. Examples of long arm deletion of other chromosomes include long arm deletion of chromosome 7 and chromosome 20. Other examples showing similar positive patterns and negative patterns include 7q31 (deletion), p16 (9p21 deletion analysis), IRF-1 (5q31) deletion, D20S108 (20q12) deletion, D13S319 (13q14) deletion, 4q12 deletion, ATM (11q22.3) deletion, and p53 (17p13.1) deletion.

Another exemplary embodiment can be applied to trisomy of chromosome 8. The first fluorescently labeled probe binds to, for example, the centromere of chromosome 8. In the positive pattern, there are three first bright spots. In the negative pattern, there are two first bright spots. Such a bright spot pattern is the same for trisomy of chromosome 12. In chromosome 7 monosomy, for example, in the case of using the first fluorescently labeled probe that binds to the centromere of chromosome 7, the positive pattern has one first bright spot. In the negative pattern, there are two first bright spots.

What is claimed is:

1. A cell analysis method comprising:
   capturing a fluorescence image of a cell in a sample which is pretreated with a fluorescent dye;
   extracting at least two bright spots in the fluorescence image including a target site;
   changing a pixel value of at least one of the extracted bright spots such that a difference of pixel values between the extracted bright spots are relatively reduced; and
   displaying the fluorescence image with the pixel value changed.

2. The cell analysis method according to claim 1, wherein
   in the extracting, a first bright spot with a first pixel value and a second bright spot with a second pixel value which is brighter than the first bright spot are extracted, and
   in the changing, at least the first pixel value is increased to make the first bright spot brighter.

3. The cell analysis method according to claim 2, wherein the first and second pixel values are increased with different change rates.

4. The cell analysis method according to claim 3, wherein the first pixel value is increased with a first change rate and the second pixel value is increased with a second change rate, and
   the first change rate is greater than the second change rate.

5. The cell analysis method according to claim 1, wherein, in the changing, one or more bright spots having pixel values less than a threshold value are changed in their pixel values.

6. The cell analysis method according to claim 1, wherein, in the changing, one or more bright spots having pixel values less than a threshold value are changed in their pixel values with a first change rate so as to increase a brightness, and
one or more bright spots having pixel values equal to or more than the threshold value are unchanged or changed in their pixel values with a second change rate which is smaller than the first change rate.

7. The cell analysis method according to claim 1, further comprising decreasing pixel values of background pixels.

8. The cell analysis method according to claim 1, wherein the target site of the first fluorescence image is a BCR locus and the target site of the second fluorescence image is an ABL locus.

9. A cell analysis method comprising:
capturing first and second fluorescence images of a cell in a sample which is pretreated with first and second fluorescent dyes, the first fluorescence image being a first color based and the second fluorescence image being a second color based;
extracting one or more first-color bright spots in the first fluorescence image;
extracting one or more second-color bright spots in the second fluorescence image; and
changing a pixel value of at least either of the first-color bright spots or the second-color bright spots based on a pixel value of the other such that a difference of pixel values between the one of first-color bright spots and one of the second-color bright spots are relatively reduced.

10. The cell analysis method according to claim 9, wherein
in the changing, a pixel value of at least either of the first-color bright spots or the second-color bright spots with a lower maximum value of pixel value is adjusted.

11. The cell analysis method according to claim 9, wherein
in the changing, a pixel value of at least either of the first-color bright spots or the second-color bright spots with a lower maximum value of pixel value is adjusted such that the maximum values of the first-color bright spots and the second-color bright spots are match.

12. A fluorescence image analyzing apparatus comprising:
a light source to emit light to a sample pretreated with a fluorescent dye;
an imaging unit to capture a fluorescence image of a cell irradiated with the light;
a processing unit that processes the fluorescence image captured by the imaging unit; and
a display unit to display the fluorescence image processed by the processing unit,
wherein the processing unit performs:
extracting at least two bright spots in the fluorescence image including a target site;
changing a pixel value of at least one of the extracted bright spots such that a difference of pixel values between the extracted bright spots are relatively reduced; and
causing the display unit to display the fluorescence image with the pixel value changed.

13. The fluorescence image analyzing apparatus according to claim 12, wherein
the processing unit extracts a first bright spot with a first pixel value and a second bright spot with a second pixel value which is brighter than the first bright spot, and the processing unit increases at least the first pixel value to make the first bright spot brighter.

14. The fluorescence image analyzing apparatus according to claim 13, wherein the first and second pixel values are increased with different change rates.

15. The fluorescence image analyzing apparatus according to claim 14, wherein the first pixel value is increased with a first change rate and the second pixel value is increased with a second change rate, and
the first change rate is greater than the second change rate.

16. The fluorescence image analyzing apparatus according to claim 12, wherein the processing unit changes pixel values of one or more bright spots having pixel values less than a threshold value.

17. The fluorescence image analyzing apparatus according to claim 12, wherein the processing unit changes pixel values of one or more bright spots having pixel values less than a threshold value with a first change rate so as to increase a brightness, and
one or more bright spots having pixel values equal to or more than the threshold value are unchanged or changed in their pixel values with a second change rate which is smaller than the first change rate.

18. The fluorescence image analyzing apparatus according to claim 12, the processing unit further performs decreasing pixel values of background pixels.

19. A fluorescence image analyzing apparatus comprising:
a light source to emit light to a sample pretreated with a fluorescent dye;
an imaging unit to capture a fluorescence image of a cell irradiated with the light;
a processing unit that processes the fluorescence image captured by the imaging unit; and
a display unit to display the fluorescence image processed by the processing unit,
wherein the processing unit performs:
capturing first and second fluorescence images of a cell in a sample which is pretreated with first and second fluorescent dyes, the first fluorescence image being a first color based and the second fluorescence image being a second color based;
extracting one or more first-color bright spots in the first fluorescence image;
extracting one or more second-color bright spots in the second fluorescence image; and
changing a pixel value of at least either of the first-color bright spots or the second-color bright spots based on a pixel value of the other such that a difference of pixel values between the one of first-color bright spots and one of the second-color bright spots are relatively reduced.

20. The fluorescence image analyzing apparatus according to claim 19, wherein
the processing unit adjusts a pixel value of at least either of the first-color bright spots or the second-color bright spots with a lower maximum value of pixel value.

21. The fluorescence image analyzing apparatus according to claim 19, wherein
the processing unit adjusts a pixel value of at least either of the first-color bright spots or the second-color bright spots with a lower maximum value of pixel value such that the maximum values of the first-color bright spots and the second-color bright spots are match.

* * * * *